(12) United States Patent
Keul et al.

(10) Patent No.: US 7,728,069 B2
(45) Date of Patent: Jun. 1, 2010

(54) REACTIVE CYCLIC CARBONATES AND UREAS USED FOR MODIFYING BIOMOLECULES, POLYMERS, AND SURFACES

(75) Inventors: Helmut Keul, Aachen (DE); Martin Möller, Aachen (DE); Nicolas Pasquier, Bulle (CH); Luc Ubaghs, Maastricht (NL)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 10/582,053

(22) PCT Filed: Dec. 9, 2004

(86) PCT No.: PCT/EP2004/014047

§ 371 (c)(1),
(2), (4) Date: Oct. 11, 2006

(87) PCT Pub. No.: WO2005/058863

PCT Pub. Date: Jun. 30, 2005

(65) Prior Publication Data

US 2007/0092656 A1    Apr. 26, 2007

(30) Foreign Application Priority Data

Dec. 9, 2003    (EP) .................... 03028224

(51) Int. Cl.
A61K 47/48 (2006.01)
C08L 89/00 (2006.01)
C07D 317/08 (2006.01)
C07D 319/06 (2006.01)

(52) U.S. Cl. .................. 525/54.1; 549/229; 549/369

(58) Field of Classification Search ............... 525/54.1; 549/269, 369

See application file for complete search history.

(56) References Cited

U.S. PATENT DOCUMENTS 4,652,667 A * 3/1987 Green ................. 558/277

(Continued)

FOREIGN PATENT DOCUMENTS

JP    2003012725 A *  1/2003

(Continued)

OTHER PUBLICATIONS

Machine Translation of JP 2003012725.*

(Continued)

*Primary Examiner*—Mark Eashoo
*Assistant Examiner*—Liam J Heincer
(74) *Attorney, Agent, or Firm*—Connolly Bove Lodge & Hutz LLP

(57) ABSTRACT

Disclosed are reactive cyclic carbonates and ureas of formula (I) or (II), wherein R and X have the meaning indicated in the description. Said carbonates and ureas allow functional groups to be specifically introduced into biomolecules, polymers, and surfaces in mild conditions.

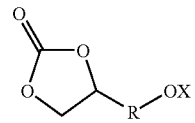

(I)

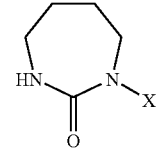

(II)

11 Claims, 1 Drawing Sheet (A)

(B)

(C)

(D)

(E)

U.S. PATENT DOCUMENTS

| | | | |
|---|---|---|---|
| 4,713,188 A * | 12/1987 | Wollenberg | 508/222 |
| 4,720,569 A * | 1/1988 | Tominaga | 560/26 |
| 5,047,261 A * | 9/1991 | Moussa et al. | 427/508 |
| 5,245,032 A * | 9/1993 | King | 544/162 |
| 5,637,655 A * | 6/1997 | Priddy et al. | 525/438 |
| 5,650,234 A | 7/1997 | Dolence et al. | |
| 5,874,509 A * | 2/1999 | Shalaby et al. | 526/194 |
| 6,084,038 A * | 7/2000 | Ohrbom et al. | 525/481 |
| 6,090,891 A * | 7/2000 | Frischinger et al. | 525/111 |
| 6,162,769 A * | 12/2000 | Polhaar et al. | 508/339 |
| 6,177,514 B1 * | 1/2001 | Pathak et al. | 525/54.1 |
| 6,407,199 B1 * | 6/2002 | Hirata et al. | 528/196 |
| 6,447,952 B1 * | 9/2002 | Spiegel et al. | 429/218.1 |
| 6,627,761 B2 * | 9/2003 | Klein et al. | 549/229 |
| 6,824,848 B2 * | 11/2004 | Dhaler et al. | 428/40.1 |
| 6,849,665 B2 * | 2/2005 | Frenz et al. | 521/64 |
| 6,887,946 B2 * | 5/2005 | Fukada et al. | 525/437 |
| 6,998,078 B2 * | 2/2006 | Wierer et al. | 264/83 |
| 2002/0006558 A1 * | 1/2002 | Kobayashi et al. | 430/7 |
| 2002/0038041 A1 * | 3/2002 | Clements et al. | 549/525 |
| 2002/0040110 A1 * | 4/2002 | Webster et al. | 525/400 |
| 2002/0183474 A1 | 12/2002 | Klein et al. | |
| 2003/0097961 A1 * | 5/2003 | Yatake et al. | 106/31.59 |
| 2003/0134926 A1 * | 7/2003 | Fukada et al. | 522/81 |
| 2003/0139556 A1 * | 7/2003 | Wagener et al. | 527/201 |
| 2003/0149127 A1 * | 8/2003 | Jansen et al. | 522/178 |
| 2003/0186013 A1 * | 10/2003 | Dhaler et al. | 428/40.1 |
| 2003/0193042 A1 * | 10/2003 | Go et al. | 252/500 |
| 2004/0091426 A1 * | 5/2004 | Schmitt-Willich et al. | 424/9.322 |
| 2004/0127608 A1 * | 7/2004 | Pardoen et al. | 524/88 |
| 2004/0236119 A1 * | 11/2004 | Van Holen | 549/229 |
| 2005/0118105 A1 * | 6/2005 | Platzek et al. | 424/9.322 |
| 2006/0029782 A1 * | 2/2006 | Harren et al. | 428/212 |
| 2007/0066754 A1 * | 3/2007 | Loeker et al. | 525/127 |

FOREIGN PATENT DOCUMENTS

WO     WO-02/42383     5/2002

OTHER PUBLICATIONS

Jansen, J. F. G. A. et al., "Fast Monomers: Factors Affecting the Inherent Reactivity of Acrylate Monomers in Photoinitiated Acrylate Polymerization", Macromolecules, 2003, vol. 36, pp. 3861-3873.

Joshi, V. P. et al., "Novel Separation Strategies Based on Molecularly Imprinted Adsorbents", Chemical Engineering Science, 1998, vol. 53, pp. 2271-2284.

* cited by examiner

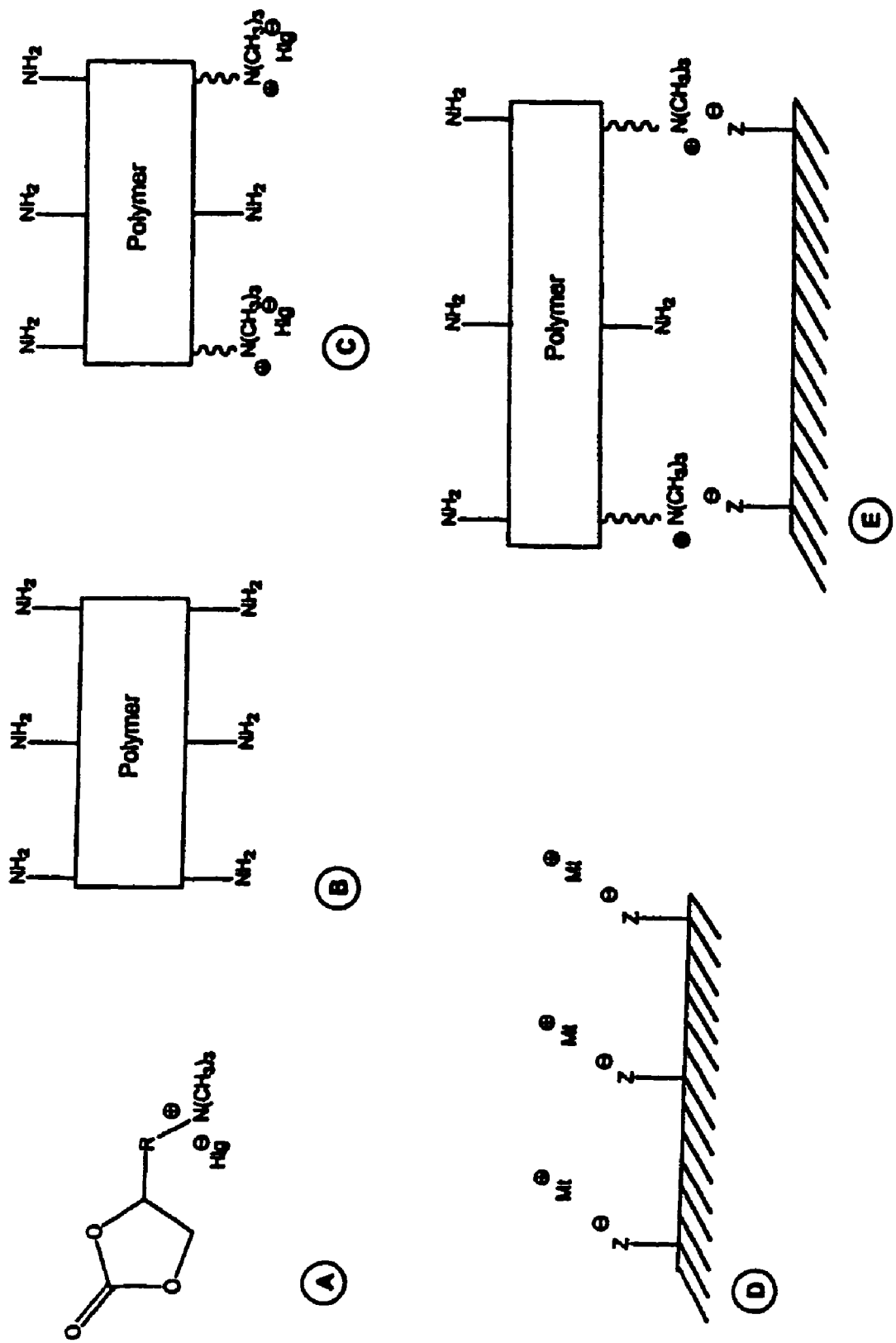

REACTIVE CYCLIC CARBONATES AND UREAS USED FOR MODIFYING BIOMOLECULES, POLYMERS, AND SURFACES

RELATED APPLICATIONS

This application is a national stage application (under 35 U.S.C. 371) of PCT/EP2004/014047 filed Dec. 9, 2004, which claims priority to European application 03028224.8 filed Dec. 9, 2003.

Reactive cyclic carbonates and ureas used for modifying biomolecules, polymers and surfaces The present invention relates to a process for modifying substrates, such as biomolecules, polymers and surfaces, with reactive cyclic carbonates and ureas, and cyclic carbonates and ureas and modified polymers.

The permanent functionalization of material surfaces is important for a multiplicity of materials and applications. For example, material surfaces can be made biocompatible by coating with heparin. Other applications are dirt-repellant and bacteriostatic treatments and improvement of the adhesion of adhesives and finishes.

The modification of a surface can be effected either reactively by formation of covalent bonds or by chemisorption or adsorption. Examples of a reactive modification are those with isocyanates, with silanes and by free radical grafting reactions. A frequently used method for introducing functional groups on surfaces makes use of coating with functional silanes, in particular aminosilanes. The treatment with aminosilanes is technically complicated and cannot be effected from aqueous solution.

Chemisorption is based on ionic interactions between negative surface charges and cationic compounds, for example ammonium compounds. Negatively charged groups are found on the surface of virtually all materials. In the case of hydrophobic polymers, such as polyolefins, negative surface charges form through oxidation in air; these can be amplified artificially by a plasma treatment or UV oxidation. Polycationic polymers, such as polyammonium compounds, adsorb onto such surfaces by polyelectrolyte complex formation. The cooperativeness of the multiple ion pair formation results in a very strong bond which is stable even at high ionic strengths and extreme pH values.

The specific modification of biomolecules is also desirable in many cases. Thus, the biological half-life of various active substances can be improved, for example, by adding polyoxyalkylene radicals.

There is a need for reagents and processes which make it possible to introduce certain chemically functional groups into biomolecules and surfaces in a specific manner. The reactions involved should take place under mild conditions and, where biomolecules are involved, without the denaturing thereof.

U.S. Pat. No. 5,650,234 describes mixed polyethylene glycol carbonates which react smoothly with amino groups in aminoglycans or proteins or surfaces containing amino groups. The polyethylene glycol carbonates permit the covalent bonding of biomolecules to surfaces.

Furthermore, there is a need for easily obtainable polycationic compounds for surface treatment, which can be applied from aqueous solutions and comprise certain functional groups or permit subsequent further modification.

Jansen, I.F.G.A. et. al., in Macromolecules 2003, 36, 3861-3873 investigate the reactivity of various acrylates, such as 2-oxo-1,3-dioxolan-4-yl methacrylate.

WO 02/42383 describes radiation-curable compositions which may comprise 2-oxo-1,3-dioxolan-4-yl methoxycarbonylaminoethyl acrylate.

The invention relates, in a first aspect, to a process for modifying a substrate which has functional groups which are selected from hydroxyl groups and primary and secondary amino groups, in which at least one substrate is brought into contact with a compound of the formula I or II under conditions such that the functional groups react, with opening of the 1,3-dioxolane ring or 1,3-diazaheptane ring and formation of a covalent bond, with the compound of the formula I or II

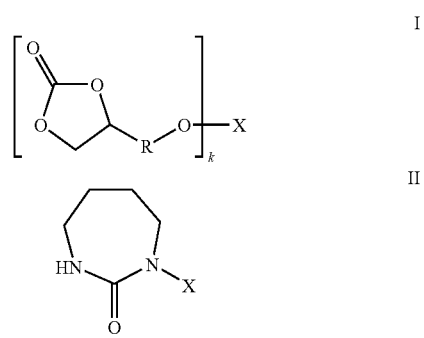

in which

R is $C_1$-$C_{12}$-alkylene;

if k is 1, X is CO—CH=$CH_2$, CO—C($CH_3$)=$CH_2$, CO—O-aryl, $C_2$-$C_6$-alkylene-$SO_2$—CH=$CH_2$ or CO—NH—$R^1$; and $R^1$ is $C_1$-$C_{30}$-alkyl, $C_1$-$C_{30}$-haloalkyl, $C_1$-$C_{30}$-hydroxyalkyl, $C_1$-$C_6$-alkoxy-$C_1$-$C_{30}$-alkyl, $C_1$-$C_6$-alkylcarbonyloxy-$C_1$-$C_{30}$-alkyl, amino-$C_1$-$C_{30}$-alkyl, mono- or di($C_1$-$C_6$-alkyl)amino-$C_1$-$C_{30}$-alkyl, ammonio-$C_1$-$C_{30}$-alkyl, polyoxyalkylene-$C_1$-$C_{30}$-alkyl, polysiloxanyl-$C_1$-$C_{30}$-alkyl, (meth)acryloyloxy-$C_1$-$C_{30}$-alkyl, sulfono-$C_1$-$C_{30}$-alkyl, phosphono-$C_1$-$C_{30}$-alkyl, di($C_1$-$C_6$-alkyl)phosphono-$C_1$-$C_{30}$-alkyl, phosphonato-$C_1$-$C_{30}$-alkyl, di($C_1$-$C_6$-alkyl)phosphonato-$C_1$-$C_{30}$-alkyl or a saccharide radical and, if k is an integer of more than 1, X is (i) the radical of a polyamine to which the moiety in brackets in the formula is bonded via (CO)NH groups, or (ii) a polymeric skeleton to which the moiety in brackets in the formula is bonded via (CO), NH—$C_2$-$C_6$-alkylene-O(CO) or (CO)—O—$C_2$-$C_6$-alkylene-O(CO) groups.

In formula I, k is 1 or an integer of more than 1, e.g. 2 or 3, or 2-10 000, such as 10-1000.

The substrate is preferably a biomolecule, a polymer or a surface.

In an embodiment of the process, the compound of the formula I or II is brought into contact with a first substrate under conditions such that a covalent bond forms between a first end of the compound of the formula I or II and the first substrate, and the reaction product is brought into contact with a second substrate under conditions such that a covalent bond forms between a second end of the compound of the formula I or II and the second substrate.

In this embodiment, the radical X generally comprises a functional group which can react with the first substrate, preferably a (meth)acryloyl, aryloxy, vinylsulfonyl or haloalkyl group.

The first and second substrates are, for example, in pairs, a surface and a biomolecule, a biomolecule and a modifier or a surface and a modifier. A modifier may be a low molecular weight or polymeric compound which imparts certain hydrophilic or lipophilic properties, solubility, stability or the like, or a directive molecule.

The invention relates, in a second aspect, to compounds of the general formula I or II

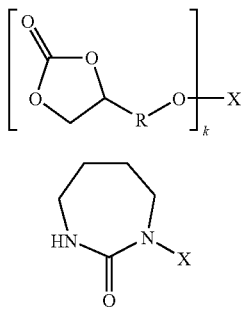

in which

R is $C_1$-$C_{12}$-alkylene, preferably $C_1$-$C_4$-alkylene, in particular methylene;

if k is 1, X is $C_2$-$C_6$-alkylene-$SO_2$—CH=$CH_2$ or CO—NH—$R^1$; and $R^1$ is $C_1$-$C_{30}$-alkyl, $C_1$-$C_{30}$-haloalkyl, $C_1$-$C_{30}$-hydroxyalkyl, $C_1$-$C_6$-alkoxy-$C_1$-$C_{30}$-alkyl, $C_1$-$C_6$-alkylcarbonyloxy-$C_1$-$C_{30}$-alkyl, amino-$C_1$-$C_{30}$-alkyl, mono- or di($C_1$-$C_6$-alkyl)amino-$C_1$-$C_{30}$-alkyl, ammonio-$C_1$-$C_{30}$-alkyl, polyoxyalkylene-$C_1$-$C_{30}$-alkyl, polysiloxanyl-$C_1$-$C_{30}$-alkyl, sulfono-$C_1$-$C_{30}$-alkyl, phosphono-$C_1$-$C_{30}$-alkyl, di($C_1$-$C_6$-alkyl)phosphono-$C_1$-$C_{30}$-alkyl, phosphonato-$C_1$-$C_{30}$-alkyl, di($C_1$-$C_6$-alkyl)phosphonato-$C_1$-$C_{30}$-alkyl or a saccharide radical and, if R is $C_2$-$C_{12}$-alkylene, in particular $C_4$-alkylene, X may also be CO-aryl, CO—CH=$CH_2$, CO—C($CH_3$)=$CH_2$ or (meth)acryloyloxy-$C_1$-$C_{30}$-alkyl-NH—CO.

If k is an integer of more than 1, X is the radical of a polyamine to which the moiety in brackets in the formula is bonded via (CO)NH groups. Examples of polyamines are alkylenediamines, dialkylenetriamines, polydimethylsiloxanes having aminoalkyl groups (terminally or as side groups), polyvinylamine, polyallyamine, polyethylenimine, chitosan, polyamide/epichlorohydrin resins, polyaminostyrene, peptides or proteins.

The term "alkyl" is intended to include straight-chain, branched and cyclic alkyl groups having 1 to 30, preferably 1 to 18, in particular 1 to 12, carbon atoms.

The term "aryl" preferably means phenyl or naphthyl which is optionally substituted by 1 to 3 $C_1$-$C_4$-alkyl or $C_1$-$C_4$-alkoxy groups.

The term "haloalkyl" means an alkyl group in which one or more or all hydrogen atoms are replaced by halogen, in particular fluorine. The term "hydroxyalkyl" means an alkyl group in which one or more hydrogen atoms are replaced by hydroxyl groups. In the same way, the terms "alkoxyalkyl", "alkylcarbonyloxyalkyl", "aminoalkyl", "ammonioalkyl", "polyoxyalkylenealkyl", "polysiloxanylalkyl", "(meth)acryloyloxyalkyl", "sulfonoalkyl", "phosphonoalkyl" and "phosphonatoalkyl" mean an alkyl radical in which one or more hydrogen atoms are replaced by an alkoxy group, an alkylcarbonyloxy group, an amino group, an ammonio group ($NR^3_3{}^+$; in which each $R^3$ independently is, for example, $C_1$-$C_{18}$-alkyl or benzyl), a polyoxyalkenyl radical, a polysiloxanyl radical, a (meth)acryloyloxy group, a sulfo group ($SO_3H$), a phosphonic acid group ($PO_3H_2$) or a phosphoric acid ester group ($OPO_3H_2$). If $R^1$ is ammonioalkyl, the compound is accompanied by one equivalent of an anion, preferably of a physiologically tolerated anion, such as a halide, e.g. chloride or bromide, sulfate, hydrogen sulfate, methosulfate, nitrate or the like.

The polyoxyalkylene radical is preferably derived from ethylene oxide and/or propylene oxide, in particular from ethylene oxide. It may be terminated at the distal end, for example, by a hydroxyl, alkoxy or alkaryloxy group. The polysiloxanyl radical is preferably derived from polydimethylsiloxanes.

The saccharide radical is, for example, a glucosyl radical.

The term "biomolecule" includes all molecules which are isolated from biological systems and/or can interact with biological systems or parts thereof. These include in particular peptides, proteins, proteoglycans, enzymes, marker substances, antibodies, receptor molecules, antigens and active substances. Specific examples are heparin, tissue plasminogen activator, streptokinase, prostaglandins and the like.

In preferred embodiments, $R^1$ is
—$(CH_2)n$—$CH_3$,
—$(CH_2)_n(CF_2)_m$—$CF_3$—
—$(CH_2)_n$—[$Si(CH_3)_2$—O]$_{p]-H}$,
—$(CH_2)_n$—$Si(OSi(CH_3)_3)_3$,
—$(CH_2)_n$—(O—$CH_2$—$CHR^4$)$_p$—$OR^3$,
—$R^2$—OH,
—$R^2$—$NH_2$,
—$R^2$—$NR^3_3$+$Y^-$
—$R^2$—$SO_3H$,
—$R^2$—$PO_3H_2$,
—$R_2$—$OPO_3H_2$,
or a saccharide radical, $R^2$ being $C_1$-$C_{18}$-alkylene, $R^3$ being $C_1$-$C_{18}$-alkyl or benzyl and $R^4$ being hydrogen or methyl, Y is one equivalent of an anion such as those mentioned above, n and m, independently of one another are an integer from 0 to 12; and p is an integer from 1 to 100, preferably from 2 to 50.

The compounds can be prepared in various ways using standard processes of organic synthesis. Preferred methods of preparation are illustrated in the examples.

Compounds of the formula I in which X is (meth)acryloyl can be obtained by reacting 2-oxo-1,3-dioxolan-4-ylalkanols with (meth)acryloyl chloride; compounds of the formula I in which X is —$CH_2$—$CH_2$—$SO_2$—CH=$CH_2$ can be obtained by reacting 2-oxo-1,3-dioxolan-4-ylalkanols with divinyl sulfone.

Compounds of the formula I in which X is a polymeric skeleton can be obtained by free radical polymerization or controlled free radical polymerization, for example by ATRP (atom transfer radical polymerization), of compounds in which X comprises a (meth)acryloyl group. Comonomers are preferably concomitantly used, such as $C_1$-$C_{12}$-alkyl (meth)acrylates, in particular methyl (meth)acrylate, and/or vinylaromatics, such as styrene. In a preferred embodiment, comonomers which have side groups reactive toward nucleophiles and whose reactivity is different from that of the 2-oxo-1,3-dioxolanyl radical are also concomitantly used. A preferred reactive comonomer is 2-phenoxycarbonyloxyethyl (meth)acrylate. A preferred compound of the formula I in which X is a polymeric skeleton is a copolymer of 2-oxo-1,3-dioxolan-4-ylmethyl (meth)acrylate, 2-phenoxycarbonyloxy-ethyl (meth)acrylate and methyl (meth)acrylate.

The above compounds react under mild conditions with nucleophiles, e.g. hydroxyl or amino groups of biomolecules or polymers or on substrate surfaces, with ring opening and formation of a covalent bond, as illustrated in the scheme below (in which D is the nucleophile and R' is the radical of the biomolecule, of the polymer or of the substrate surface; different nucleophiles D are illustrated in table 2 of the following examples):

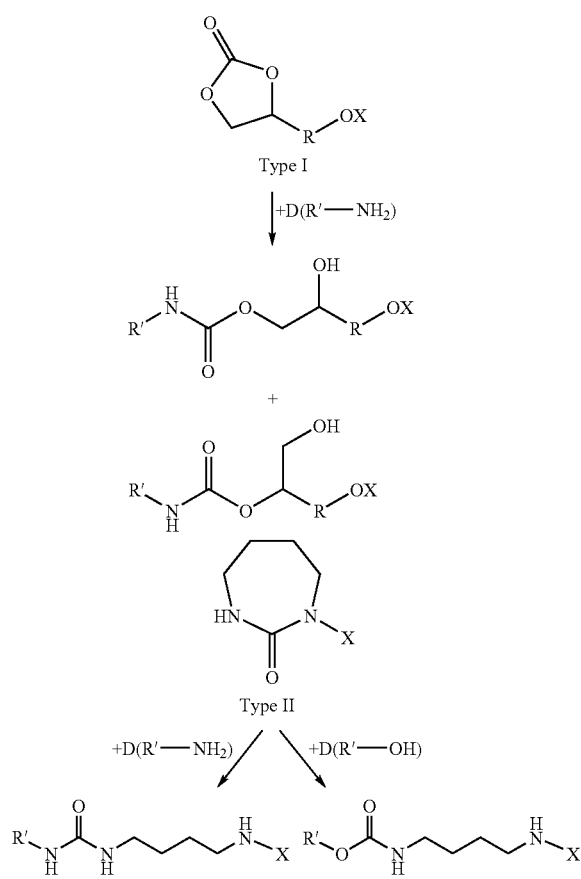

Compounds of the formula I preferably react with primary or secondary amino groups; compounds of the formula II preferably react with primary or secondary amino groups and hydroxyl groups.

In this way, the compounds according to the invention make it possible to introduce a wide range of different radicals X into biomolecules or polymers and to bind said radicals to substrate surfaces.

Surfaces which can be treated by this process are, for example, the surfaces of materials which have intrinsic amino and/or hydroxyl groups or surfaces which were treated with aminosilanes by processes known per se.

The invention furthermore relates to modified polymers, i.e. reaction products of the compounds according to the invention with a polymer which has functional groups which are selected from hydroxyl groups and primary and secondary amino groups. The reaction of the compounds according to the invention with a polyamine or a polyol permits the introduction of the functional group X into the polymer structure. Examples of polyamines are polyvinylamine, polyallylamine, polyethylenimine, chitosan, polyamide epichlorohydrin resins as sold under the name Hercosett®, polyaminostyrene, peptides or proteins, such as gelatin. Preferred proteins are modified keratin polypeptides which are enriched with lysine (2,6-diaminohexanoic acid) by reverse proteolysis (plastein reaction).

The reaction of the polymer with the compounds according to the invention is a polymer-analogous reaction. The concentration of the functional groups X in the reaction product can be established by the choice of the stoichiometric ratio of the amino or hydroxyl groups in the polymer to the reagent I or II.

In preferred reaction products, at least some of the radicals $R^1$ are ammonioalkyl, i.e. the reaction products are cationic polyelectrolytes. The cationic polyelectrolytes obtained can adhere permanently to an anionic material surface by a polyelectrolyte interaction.

The reaction is preferably carried out in such a way that not all hydroxyl and/or amino groups of the polymer participate in the reaction with the compounds according to the invention, so that the reaction products still contain reactive hydroxyl and/or primary or secondary amine functions. In this way, reactive $NH_2$, NH or OH groups which permit rapid and effective binding of different coatings can be introduced into the surfaces. Examples are epoxides, isocyanates, anhydrides and carboxylic acids as well as acrylates (Michael addition), but active substances of any type can also be immobilized on the surface in this manner.

In further preferred reaction products, some of the radicals $R^1$ are ammonioalkyl and some of the radicals $R^1$ are one or more radicals differing therefrom. In addition to the cationic groups which serve for binding/adhesion to a material surface, the reaction product has further functional groups. These can be used for anchoring different functional groups to a surface. These may be biomolecules, such as active substances, e.g. bactericides, insecticides or medicaments, which, if appropriate, become active by liberation only after hydrolytic or enzymatic degradation.

The invention relates, in a further aspect, to a process for modifying surfaces, in which the surface is brought into contact with a reaction product described above, in particular one in which at least some of the radicals $R^1$ are ammonioalkyl. The surfaces which can be treated in this manner may be those comprising any desired materials, e.g. glass, ceramic materials, metals, plastics, such as polyolefins, polystyrenes, high-impact polystyrenes. It is also possible to treat the surfaces of fibers or filaments. A particular advantage of the invention is that the coating or the application of the reaction product can be effected from an aqueous solution and requires no complicated preparation and treatment, such as, for example, the surface treatment with aminosilanes.

In addition to the direct surface coating also as sizes and finishes of fibers, the polymers thus prepared are used as dispersants and (reactive) emulsifiers. Further applications in the area of polymeric additives relate to adhesion promoters, adhesives, contact adhesives and the immobilization of active substances.

The invention is illustrated in more detail by the attached figure and the following examples.

FIG. 1 schematically shows the production of a polycationic material surface modified according to the invention. (A) designates the compound of the formula I (in which R is, for example, —$CH_2$—OCONH—$(CH_2)_3$— and $Hlg^-$ is a halide) which is used according to the invention and has an ammonium substituent. The reaction with the polyamine (B) leads to the reaction product (C). (D) shows a material surface having negative surface charges $Z^-$, which are loosely associated with cations $Mt^+$. On treatment of the material surface (D) with the reaction product (C), the salt $Mt^+Hlg^-$ is displaced and, owing to the multiple ion pair interaction, strong adhesion of the polymer to the surface forms. Amino groups (—$NH_2$) are available on the polymer for further modifications.

EXAMPLE 1

Compound A.1

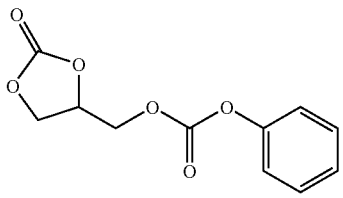

The compound can be obtained by the method described by J.F.G.A. Jansen, A. A. Dias, M. Dorschu, B. Coussens, Macromolecules 2003, 36, 3861-3873.

Compound A.2

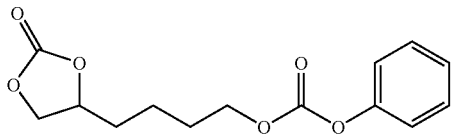

In a three-necked flask provided with a magnetic stirrer, dropping funnel and reflux condenser, 27 g (202 mmol) of 1,2,6-hexanetriol are dissolved in 65 ml of 1,4-dioxane. At 0° C., 126.5 g; 101.7 ml (808 mmol; 4.0 eq.) of phenyl chloroformate are added dropwise in a period of about 1 h and then a solution of 44 ml (313 mmol) of triethylamine in 200 ml of toluene is slowly added dropwise over a period of 3 h. After the end of the addition, stirring is effected for 16 h at room temperature to complete the reaction. Thereafter, 68 ml of 1 M HCl solution are added dropwise to the now turbid solution, and the reaction solution is taken up with about 300 ml of ethyl acetate. The organic phase is washed in succession with 1 M HCl solution and H₂O and dried over Na₂SO₄, the drying agent is filtered off and the solvent is distilled off. A yellowish oil with an odor of phenol remains behind. The phenol is removed by means of condensation at 70° C. under a high vacuum. The diphenyl carbonate formed as byproduct is extracted from the brown-yellow oil by means of Soxlett extraction. For this purpose, the oil is taken up in three times the amount of silica gel, introduced into a Soxlett tube and extracted for 16 h with pentane. The product is dissolved by treating the silica gel with ethyl acetate, and the light yellow, highly viscous oil is dried under a high vacuum with stirring for 16 h. Yield: 32 g (114 mmol; 56% of theory).

¹H-NMR (300 Mhz, DMSO-$d_6$):

$\delta_H$=1.46 (m, 2H, $CH_2$-5); 1.71 (m, 4H, $CH_2$-4, $CH_2$-6); 4.14 (d/d, 1H, $CH_2$-2$^a$, $^3J$=8.3 Hz, $^3J$=7.9 Hz); 4.22 (t, 2H, $CH_2$-7, $^3J$=6.4 Hz); 4.58 (t, 1H, $CH_2$-2$^b$, $^3J$=8.3 Hz); 4.79 (qu, 1H, CH-3, $^3J$=7.2 Hz); 7.25 (d, 2H, CH-10, $^3J$=7.2 Hz); 7.29 (d, 1H, CH-12, $^3J$=7.5 Hz); 7.44 (d/d, 2H, CH-11, $^3J$=7.9 Hz, $^3J$=7.5 Hz)ppm.

¹³C-NMR Spectrum (75 MHz, DMSO-$d_6$):

$\delta_c$=20.39 (C-5, 1C); 27.55 (C-6, 1C); 32.33 (C-4, 1C); 68.16 (C-7, 1C); 69.12 (C-2, 1C); 76.85 (C-3, 1C); 121.12 (C-10, 2C); 126.06 (C-12, 1C); 129.55 (C-11, 2C); 150.74 (C-9, 1C); 153.06 (C-8, 1C); 154.87 (C-1, 1C)ppm.

Compound B (phenyl 2-oxo-[1,3]diazepan-1-carbonate)

The compound was prepared as follows: First 1.5 equivalents of triethylamine and then, slowly at from 0 to 50° C., phenyl chloroformate (1.5 equivalents) were added to a solution of trimethyleneurea (1 equivalent) in dichloromethane. After the end of the addition, stirring was effected for a further 30 min to 2 h. Thereafter, cooling was effected and the precipitate (amine hydrochloride) was filtered off and washed with a little solvent. The product was purified by column chromatography (mobile phase:diethyl ether/ethyl acetate=1/1) and dried at room temperature in vacuo ($10^{-2}$ mbar). Yield: 90% of theory.

The preparation of further compounds is effected, for example, according to the following scheme:

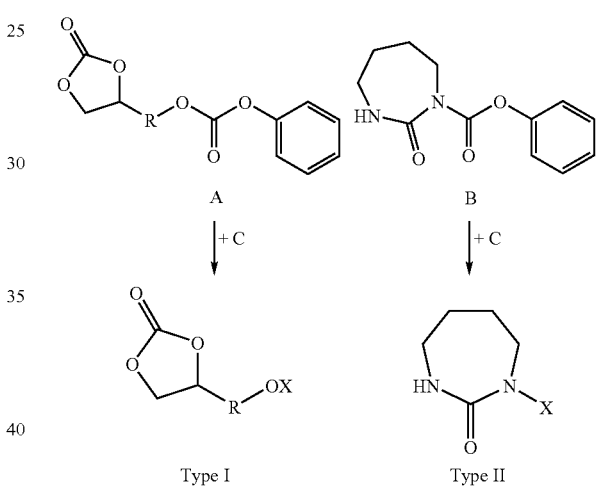

One of the components C indicated in table 1 is added in the amount indicated (in equivalents) at the temperature indicated with stirring to an initially introduced solution of component A.1 or A.2 (for the preparation of further compounds of the formula I) or component B (for the preparation of further compounds of the formula II) in a suitable solvent (e.g. chloroform, dichloromethane, ethyl acetate, diethyl sulfoxide, dimethylacetamide, dimethylformamide) in a flask of suitable size which is provided with reflux condenser and controllable stirrer. The solution is then stirred for the time indicated in table 1. The product is isolated by customary methods (distilling off the volatile constituents, precipitation and/or chromatography).

TABLE 1

| | | Preparation of type I | | | Preparation of type II | | |
|---|---|---|---|---|---|---|---|
| No. | Component C | Eq. | Temp. [° C.] | Time [h] | Eq. | Temp. [° C.] | Time [h] |
| 1 | Alkylamine | 1.0-1.5 | (−10)-50 | 1-48 | 1-5 | 0-100 | 1-48 |
| 2 | Fluoroalkylamine | 1.0-1.5 | (−10)-50 | 1-48 | 1-5 | 0-100 | 1-48 |
| 3 | Aminopolysiloxane | 1.0-1.5 | (−10)-50 | 1-48 | 1-5 | 0-100 | 1-48 |
| 4 | Polyoxyethylenemonoamine | 1.0-1.5 | (−10)-50 | 1-48 | 1-5 | 0-100 | 1-48 |
| 5 | α-Aminoalkyl-ω-alkoxypolyethyleneglycol | 1.0-1.5 | (−10)-50 | 1-48 | 1-5 | 0-100 | 1-48 |

TABLE 1-continued

| | | Preparation of type I | | | Preparation of type II | | |
|---|---|---|---|---|---|---|---|
| No. | Component C | Eq. | Temp. [° C.] | Time [h] | Eq. | Temp. [° C.] | Time [h] |
| 6 | Aminoalcohol | 1.0-1.5 | (−10)-50 | 1-48 | 1-5 | 0-100 | 1-48 |
| 7 | Diamine | — | — | — | 5-10 | 0-100 | 1-48 |
| 8 | Aminoalkyl (alkyl)acrylate | 1.0-1.5 | (−10)-50 | 1-48 | 1-5 | 0-100 | 1-48 |
| 9 | Aminomonosaccharide (glucosamine) | 1.0-1.5 | (−10)-50 | 1-48 | 1-5 | 0-100 | 1-48 |
| 10 | Aminoalkylphosphonic acid | 1.0-1.5 | (−10)-50 | 1-48 | 1-5 | 0-100 | 1-48 |
| 11 | Monoaminoalkyl phosphate | 1.0-1.5 | (−10)-50 | 1-48 | 1-5 | 0-100 | 1-48 |
| 12 | Aminoalkanesulfonic acid | 1.0-1.5 | (−10)-50 | 1-48 | 1-5 | 0-100 | 1-48 |
| 13 | Aminoalkyltrialkylammonium salt | 1.0-1.5 | (−10)-50 | 1-48 | 1-5 | 0-100 | 1-48 |

Compound I.1 (R = $CH_2$, X = CO—NH—$(CH_2)_3$—N$(CH_3)_2$

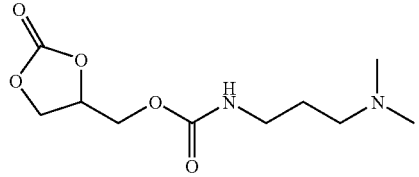

10 g (42 mmol) of A.1 are dissolved in 100 ml of THF in a two-necked flask provided with an internal thermometer and dropping funnel. At 0C, a solution of 4 g (40 mmol) of 3,3-dimethylaminopropylamine in 50 ml of THF is added slowly so that the temperature does not exceed 5° C. To complete the reaction, the reaction solution is stirred for a further 16 h. The temperature is allowed to increase slowly to room temperature. The reaction batch is evaporated down in a rotary evaporator. For removing phenol, the residue is taken out with 200 ml of a mixture of THF/$Et_2O$ (1:1) and this is extracted 5 times with 50 ml of $H_2O$ each time. The combined aqueous phases are extracted 5 times with 70 ml of $CHCl_3$ each time. The organic phase is dried over $Na_2SO_4$, the drying agent is filtered off and the solvent is distilled off by means of a rotary evaporator. The colorless, highly viscous oil is dried with stirring under a high vacuum over night. Yield: 5.1 g (21 mmol; 50%)

$^1$H-NMR (300 MHz, $CDCl_3$):

$\delta_H$=1.67 (qu, 2H, $CH_2$-7, $^3J$=6.8 Hz); 2.22 (s, 6H, $CH_3$-9); 2.35 (t, 2H, $CH_2$-8, $^3J$=6.8 Hz); 3.24 (q, 2H, $CH_2$-6, $^3J$=6.0 Hz), 4.30 (m, 2H, $CH_2$-4); 4, 36 (d/d, 1H, $CH_2$-$2^a$, $^3J$=8.7 Hz, $^3J$=6.0 Hz); 4.55 (t, 1H, $CH_2^b$-2, $^3J$=8.3 Hz); 4.92 (qu, 1H, CH-3, $^3J$=7.2 Hz); 6.2 (s, br., 1H, NH) ppm.

$^{13}$C-NMR-Spektrum (75 MHz, CDCl3):

δc=26.69 (C-7, 1C); 40.52 (C-6, 1C); 45.34 (C-9, 2C); 57.90 (C-8, 1C); 63.24 (C-4, 1C); 66.04 (C-2, 1C); 74.55 (C-3, 1C); 154.78 (C-1, 1C); 155.68 (C-5, 1C)ppm.

Compound I.2 (R=$CH_2$, X=CO—NH—$(CH_2)_2$—N$(CH_3)_2$

Starting from 20.1 mmol of A.1 and 23 mmol of dimethylaminoethylamine, the product was obtained in 63% yield.

Compound I.3 (R=$CH_2$, X=CO—NH—$(CH_2)_3$—$CH_3$)

Starting from 20.1 mmol of A.1 and 23 mmol of butylamine, the product was obtained in 80% yield.

Compound I.4 (R=$CH_2$, X=CO—NH—$(CH_2)_{11}$—$CH_3$)

Dicarbonate A.1 (2.00 g, 8.40 mmol) was dissolved in 20 ml of dry THF in a two-necked flask equipped with an internal thermometer and a dropping funnel. After cooling to 0° C., a suspension of dodecylamine (1.56 g, 8.40 mmol) in 10 ml of dry THF was slowly added and the temperature was kept below 5° C. and allowed to warm up to RT overnight. The solvent was removed in vacuo (~20 mbar, 40° C.). The cyclic carbonate functionalized with a $C_{12}$-alkyl chain was dissolved in 15 ml of $CHCl_3$ and crystallized by adding 30 ml of $Et_2O$. (Yield: 93%).

$^1$H-NMR (300 MHz, $CDCl_3$, TMS):

$\delta_H$=0.88 (t, 3H, $CH_3$-17), 1.19-1.36 (s, 18H, $CH_2$-(8-16)), 1.41-1.56 (m, 2H, $CH_2$-7), 3.16 ($d^xt$, 2H, $CH_2$-6), 4.22-4.38 (m, 3H, $CH^aH^b$-2, $CH_2$-4), 4.55 ($d^xd$, 1H, $CH^aH^b$-2), 4.86-4.95 (m, 1H, CH-3), 5.08-5.18 (b, 1H, NH) ppm.

$^{13}$C-NMR (75 MHz, $CDCl_3$, TMS):

$\delta_C$=14.1 (C-17), 22.7 (C-16), 26.7 (C-8), 29.3-29.8 (7C, C-(9-15)), 31.9(C7), 41.3 (C-6), 63.3 (C-4), 66.0 (C-2), 74.5 (C-3), 154.8 (C-1), 155.6 (C-5) ppm.

Compound I.5 (R=$CH_2$, X=CO—NH—$(CH_2)_{17}$—$CH_3$)

Dicarbonate A.1 (5.00 g, 21.0 mmol) was dissolved in 20 ml of dry THF and cooled to 0° C. in a two-necked flask equipped with an internal thermometer and a dropping funnel. A suspension of stearylamine (5.65 g, 21.0 mmol) in 20 ml of dry THF was slowly added, and the temperature was kept below 5° C. The reaction was stirred for 2 hours at 0° C. and 1.5 days at RT. The solvent was removed in vacuo (~20 mbar, 40° C.). The cyclic carbonate functionalized with a $C_{18}$-alkyl chain was recrystallized from $CHCl_3$. (Yield: 85%).

Compound I.6 (R=$CH_2$, X=CO—NH—$(CH_2)_3$—$N(CH_3)_3I$)

Compound I.6

(R = $CH_2$, X = CO—NH—$(CH_2)_3$—$N(CH_3)_3I$)

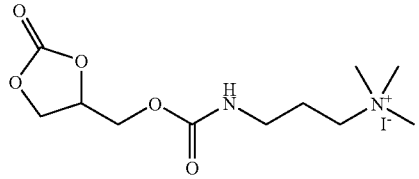

A solution of 0.70 g (5 mmol) of $CH_3I$ in 5 ml of THF is rapidly added dropwise to a solution of 0.50 g (2 mmol) of compound I.1 in 5 ml of THF. A colorless precipitate separates out during the stirring for one hour. The THF phase is decanted and the precipitate is washed several times with THF. The product obtained is dried under a high vacuum overnight. Yield: 0.77 g (1.98 mmol; 99% of theory).

$^1$H-NMR (300 Mhz, DMSO-$d_6$):

$\delta_H$=1.85 (m, 2H, $CH_2$-7); 3.08 (s, 9H, $CH_3$-9); 3.33 (m, 4H, $CH_2$-8, $CH_2$-6); 4.17-4.31 (m, 3H, $CH_2$-4, $CH_2$-$2^a$); 4.57 (t, 1H, $CH_2$-$2^b$, $^3J$=8.7 Hz); 5.04 (m, 1H, CH-3); 7.48 (t, 1H, NH) ppm.

$^{13}$C-NMR Spectrum (75 MHz, DMSO-$d_6$):

$\delta_c$=22.97 (C-7, 1C); 37.42 (C-6, 1C); (C-9, 1C); 52.26 (C-8, 1C); 63.29 (C-4, 1C); 65.95 (C-2, 1C); 74.75 (C-3, 1C); 154.72 (C-1, 1C); 155.68 (C-5, 1C) ppm.

Compound I.7 (R=$(CH_2)_4$, X=CO—NH—$(CH_2)_3$—$N(CH_3)_2$)

The compound was prepared analogously to compound I.1, the compound A.2 being used instead of the compound A.1 as starting material.

Compound I.8 (R=$CH_2)_4$, X=CO—NH—$(CH_2)_5$—$CH_3$)

The compound was prepared analogously to the compound I.3, the compound A.2 being used instead of the compound A.1 and hexylamine being used instead of butylamine as starting materials.

Compound I.9 (R=$(CH_2)_4$, X=CO—NH—$(CH_2)_{11}$—$CH_3$)

The compound was prepared analogously to the compound I.4, the compound A.2 being used instead of the compound A.1 as starting material.

Compound I.10 (R=$CH_2$, X=CO—NH—$(CH_2)_2$—$N(CH_3)_3$½$(SO_4)$)

The compound was obtained in 90% yield by reacting 14.7 mmol of the compound I.2 with 29 mmol of dimethyl sulfate.

Compound I.11 (R=$CH_2)_4$, X=CO—NH—$(CH_2)_3$—$N(CH_3)_3$1)

The compound was prepared analogously to the compound I.6, the compound I.7 being used instead of the compound I.1 as starting material.

A solution of 4.6 g (4 mmol) of nonadimethylsiloxane-dipropylamine in 50 ml of THF is slowly added dropwise at 0° C. to a solution of 3 g (13 mmol) of A.1 in 30 ml of THF. To complete the reaction, the solution is stirred for a further 48 h. The temperature is allowed to increase slowly to room temperature. The reaction batch is evaporated down in a rotary evaporator. In addition to the product, excess starting material and phenol remain behind. The impurities are removed by dissolution in pentane. The conversion of nonadimethylsiloxanedipropylamine is quantitative.

$^1$H-NMR (300 Mhz, $CDCl_3$):

$\delta_H$=0.03 (S, 6H, $CH_3$-10); 0.07 (S, 48H, $CH_3$-9); 0.53 (t, 4H, $CH_2$-8, $^3J$=8.1 Hz); 1.54 (m, 4H, $CH_2$-7); 3.16 (m, 4H, $CH_2$-6); 4.30 (m, 3H, $CH_2$-4, $CH_2$-$2^a$); 4.54 (t, 1H, $CH_2$-$2^b$, $^3J$=8.7 Hz); 4.90 (m, 2H, CH-3).

Compound I.13 (R=$(CH_2)_4$, X=CO—NH—$(CH_2)_3$—$(Si(CH_3)_2$—O$)_8$—Si—$(CH_2)_3$—NH—CO)

The compound was prepared analogously to the compound I.12, the compound A.2 being used instead of the compound A.1 as starting material.

Compound I.1.14 (R=$CH_2$, X=CO—NH—$(CH_2)_3$—$Si(OSiMe_3)_3$)

A solution of 4.41 g (12.5 mmol) of tris(trimethylsilyloxy)silanepropylamine in 50 ml of THF is slowly added dropwise at 0° C. to a solution of 3 g (12.6 mmol) of A.1 in 30 ml of THF. To complete the reaction, the reaction solution is stirred for a further 16 h. The temperature is allowed to increase slowly to room temperature. The reaction batch is evaporated down in a rotary evaporator. Yield: quantitative.

Compound I.15 (R=$CH_2$, X=CO—NH—[CH$(CH_3)CH_2O]_n(CH_2CH_2O)_m CH_3$)

A solution of 2.27 g (2.1 mmol) of Jeffamine M-1000 in 25 ml of THF is slowly added dropwise at 0° C. to a solution of 0.5 g (2.1 mmol) of A.1 in 5 ml of THF. To complete the reaction, the reaction solution is stirred for a further 72 h. The temperature is allowed to increase slowly to room temperature. The reaction batch is evaporated down in a rotary evaporator. Yield: quantitative.

Compoud I.12

(R=$CH_2$, X=CO—NH—$(CH_2)_3$—$(Si(CH_3)_2O)_8$—Si—$(CH_2)_3$—NH—CO)

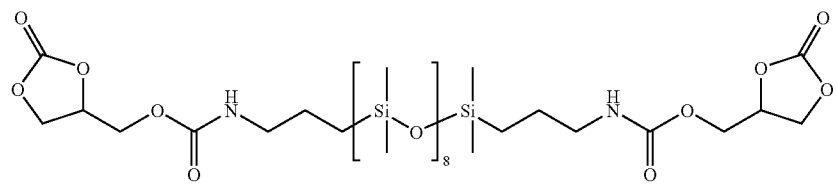

Compound I.16
(R = CH$_2$, X = CH$_2$CH$_2$SO$_2$CH=CH)

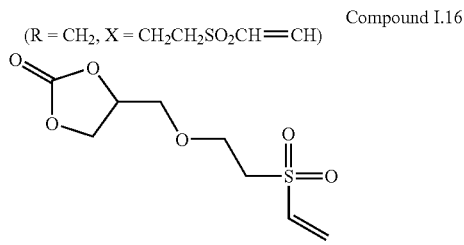

Diazabicycloundecane (25 μl) and divinyl sulfone (0.99 g, 8.40 mmol) were added to a solution of 4-(hydroxymethyl)-[1,3]dioxolan-2-one (0.2 g, 1.63 mmol) in tetrahydrofuran (5 ml) and stirring was effected for 24 h at room temperature under a nitrogen atmosphere. For purification, tetrahydrofuran is distilled off, the residue is dissolved in pentane and the product is separated off as a viscous oil by cooling to 0° C. The yield is 75%.

EXAMPLE 2

Use Examples for Compounds of the Type I and Type II

One of the components D indicated in table 2, which corresponds to one of the components C or is a nitrogen-containing polymer or a polyol, is added in the amount indicated (in equivalents based on the number of functional groups in the polymer) at the temperature indicated with stirring to a solution of a compound of the formula I or II in a suitable solvent (e.g. water, chloroform, dichloromethane, ethyl acetate, dimethyl sulfoxide, dimethylacetamide, dimethylformamide) in a flask of suitable size which is provided with a reflux condenser and controllable stirrer. The solution is then stirred over the period indicated in table 2. The product is isolated by customary methods, for example by washing, distilling off the volatile constituents, precipitation, chromatography.

TABLE 2

| | | Compound I | | | Compound II | | |
|---|---|---|---|---|---|---|---|
| No. | Component D | Eq. | Temp. [° C.] | Time [h] | Eq. | Temp. [° C.] | Time [h] |
| 1 | Component C | 0.1-5 | 20-100 | 1-48 | 0.1-5 | 75-150 | 1-48 |
| 2 | Polyallylamine | 0.1-5 | 20-100 | 1-48 | 0.1-5 | 75-150 | 1-48 |
| 3 | Polyethylenimine | 0.1-5 | 20-100 | 1-48 | 0.1-5 | 75-150 | 1-48 |
| 4 | Chitosan | 0.1-5 | 20-100 | 1-48 | 0.1-5 | 75-150 | 1-48 |
| 5 | Hercosett-like compounds | 0.1-5 | 20-100 | 1-48 | 0.1-5 | 75-150 | 1-48 |
| 6 | Polyaminostyrene | 0.1-5 | 20-100 | 1-48 | 0.1-5 | 75-150 | 1-48 |
| 7 | Protein | 0.1-5 | 20-100 | 1-48 | 0.1-5 | 75-150 | 1-48 |
| 8 | Polyol | — | — | — | 0.1-5 | 75-150 | 1-48 |

EXAMPLE 2.1

Reaction of I.12 with Dimethylaminopropylamine

A solution of 0.78 g (7.7 mmol) of dimethylaminopropylamine in 10 ml of THF is added dropwise at 66° C. to a solution of 6.27 g of compound I.12 in 50 ml of THF. To complete the reaction, the reaction solution is refluxed for a further 72 h. After removal of the solvent, a dark yellow viscous oil is obtained.

Preparation of the Quaternary Ammonium Compound 7.51 g (6 mmol) of the above product are dissolved in 25 ml of THF, and a solution of 1.7 g (12 mmol) of MeI in 5 ml of THF is added dropwise at RT. To complete the reaction, the solution is stirred for a further 3 h at RT. The solvent is distilled off in a rotary evaporator and the residue is washed with 250 ml of Et$_2$O and dried under a high vacuum overnight. The product is a brown, hygroscopic solid. Yield: quantitative.

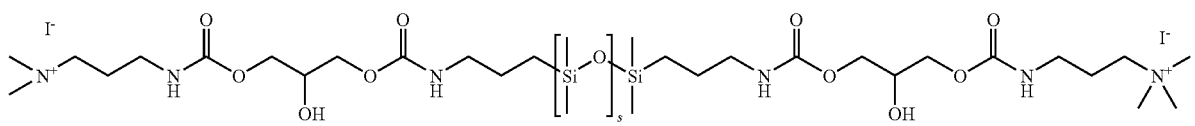

EXAMPLE 2.2

Reaction of I.13 with Dimethylaminopropylamine

The reaction and quaternization were effected analogously to example 2.1.

EXAMPLE 2.3

Reaction of I.1 with Nonadimethylsiloxanedipropylamine

A solution of 1.62 g (2 mmol) of nonadimethylsiloxanedipropylamine in 10 ml of THF is added dropwise to a solution of 1.04 g (4 mmol) of compound I.1 in 10 ml of THF, and the solution is refluxed for 96 h at 66° C. After removal of the solvent, a highly viscous yellow oil remains behind. Yield: 2.5 g (2 mmol; 100% of theory).

$^1$H-NMR (300 Mhz, CDCl$_3$):

δH=0.03 (S, 6H, CH$_3$-17); 0.07 (S, br., 48H, CH$_3$-16); 0.53 (t, 4H, CH$_2$-15); 1.52 (m, 4H, CH$_2$-14); 1.66 (qu, 4H, CH$_2$-3); 2.20 (s, 12H, CH$_3$-1); 2.34 (t, 4H, CH$_2$-2); 3.18 (d, 8H, CH$_2$-4, CH$_2$-13); 3.70 (m, 2H, CH$_2$-8); 4.13 (m, 8H, CH$_2$-7, CH$_2$-10); 5.93 (s, br., 2H, NH) ppm.

$^{13}$C-NMR Spectrum (75 MHz, CDCl$_3$):

δ$_c$=1.05 (C-16, C-17, 2C); 15.23 (C-15, 2C); 23.82 (C-14, 2C); 26.96 (C-3, 2C); 30.32; 40.30 (C-2, 2C); 44.06 (C-13, 2C); 45.36 (C-1, 4C); 57.83 (C-4, 2C); 65.83; 156.88 (C-6, C-11, 4C) ppm.

Preparation of the Quaternary Ammonium Compound 3.3 g (2.6 mmol) of the compound obtained above is dissolved in 30 ml of THF, and a solution of 0.93 g (6.6 mmol) in 10 ml of THF is added dropwise at RT. The batch is stirred for a further 3 h at RT. The solution becomes turbid, and a colorless oily phase separates out after some time. The THF phase is decanted and the oil is washed several times with THF.

For purification, the residue is dissolved in CH$_2$Cl$_2$ and precipitated with Et$_2$O. The product is filtered off and dried overnight under a high vacuum. A yellowish, hygroscopic product is obtained and is stored under $N_2$. Yield: quantitative.

$^1$H-NMR (300 Mhz, DMSO-$d_6$):

$\delta_H$=0.03 (s, 6H, $CH_3$-17); 0.07 (s, br., 48H, $CH_3$-16); 0.48 (t, 4H, $CH_2$-15); 1.40 (m, 4H, $CH_2$-14); 1.84 (m, 4H, $CH_2$-3); 2.93 (m, 8H, $CH_2$-4, $CH_2$-13); 3.27 (m, 4H, $CH_2$-2); 3.92 (t, 8H, $C_2$-7, $CH_2$-10, $^3$J=); 4.74 (s, br., 1H, OH); 5.13 (s, br., 1H, OH); 7.17 (s, br., 2H, NH-12); 7.31 (s, br., 2H, NH-5) ppm.

$^{13}$C-NMR-Spectrum (75 MHz, DMSO-$d_6$):

$\delta_c$=−0.65-0.33 (C-16, C-17, 18C); 13.80 (C-15, 2C); 22.09 (C-14, 2C); 22.31 (C-3, 2C); 36.40 (C-4, 2C); 42.3 (C-13, 2C); 51.29 (C-1, 6C); 62.38 (C-2, 2C); 63.97 (C-10, 2C); 64.22 (C-7, 2C); 65.98 (C-8, 2C); 155.09 (C-11, 2C); 155.26 (C-6; 2C).

EXAMPLE 2.4

Reaction of I.7 with Nonadimethylsiloxanedipropylamine

The reaction and quaternization were effected analogously to example 2.1.

EXAMPLE 2.5

Reaction of I.9 with Dimethylaminopropylamine

The cyclic carbonate functionalized with a $C_{12}$-alkyl chain (5.02 g, 15.2 mmol) was dissolved in $CHCl_3$ at RT, 3-dimethylaminopropylamine (2.22 g, 21.7 mmol) was added and stirring was effected under reflux for 2 days. The solvent and the excess 3-dimethylaminopropylamine were removed in vacuo. The functional diurethane was used without further purification for the quaternization of the amino group. (Yield: quantitative).

EXAMPLE 2.6

Reaction of I.5 with Dimethylaminopropylamine

The cyclic carbonate functionalized with a $C_{18}$-alkyl chain (2.50 g, 6.04 mmol) and 3-dimethylaminopropylamine (0.74 g, 7.25 mmol) were dissolved in 25 ml of $CHCL_3$ and stirred under reflux for 20 hours. The solvent was removed in vacuo, and the functional diurethane was used without further purification for the quaternization of the amino group. (Yield: quantitative).

Quaternization with MeI: A solution of MeI (15 mmol) acetone, toluene or acetonitrile (5 ml) was added dropwise to a solution of the tertiary amine (5 mmol) in the same solvent (5 ml). The reaction was stirred at RT for 2 hours. The product was precipitated (possibly with addition of hexane as precipitating agent). The product was filtered off and dried. (Yield: 85-93%)

Quaternization with n-hexyl bromide, $C_{12}H_{25}Br$, n-$C_{18}H_{37}Br$: The desired alkyl bromide (n-hexyl, n-dodecyl or stearyl bromide, 7 mmol) was added to a solution of the tertiary amine (5 mmol) in acetonitrile (10 ml). The reaction was stirred under reflux for 22 hours. The solvent was removed in vacuo. The product was purified by exchanging the opposite ion (bromide for chloride) (quantitative conversion of the amine).

Quaternization with n-hexyl-OTs, $C_{12}H_{25}$-OTs, n-$C_{18}H_{37}$-OTs: The desired alkyl tosylate (n-hexyl, n-dodecyl or stearyl tosylate, 7 mmol) was added to a solution of the tertiary amine (5 mmol) in acetonitrile (10 ml). The reaction was stirred under reflux for 20 hours. The solvent was removed in vacuo. The product was purified by exchanging the opposite ion (tosylate for chloride) (quantitative conversion of the amine).

EXAMPLE 3

Modification of Polyamines

EXAMPLE 3.1

Modification of Poly(allylamine)

Polyallylamine ($M_w$=~17 000 g/mol) in 20% strength by weight aqueous solution (1.00 g, 3.5 mmol) and a solution of the compound I.9 (288 mg, 0.875 mmol) in 4 ml of THF were mixed and were stirred for 18 hours at 80° C. After cooling, the solution was clear. After removal of THF in vacuo, the product was precipitated. NMR spectroscopic analysis showed the presence of all building blocks in the product.

EXAMPLE 3.2

Modification of Poly(ethylenimine)

Polyethylenimine ($M_w$=10 000 g/mol, Aldrich) (15.2 mmol of $NH_2$ groups) and the compound I.3 (7.6 mmol) and compound I.10 (7.6 mmol) were stirred in methanol at 70° C. (or alternatively in dimethylformamide at 80° C.) for 8 h. The product was isolated by precipitation in toluene. NMR spectroscopic analysis showed the presence of all building blocks in the product.

EXAMPLE 3.3

Modification of Poly(dimethylsiloxane-co-methylaminopropylsiloxane)

A solution of 9.45 g (2.1 mmol) of polydimethylsiloxane-co-methylpropylaminesiloxane in 80 ml of THF is slowly added dropwise at 0° C. to a solution of 0.5 g (2.1 mmol) of compound A.1 in 5 ml of THF. To complete the reaction, the reaction solution is stirred for a further 72 h. The temperature is allowed to increase slowly to room temperature. The reaction batch is evaporated down in a rotary evaporator. Yield: quantitative.

EXAMPLE 4

Copolymerization of 2-oxo-1,3-dioxolan-4-ylmethyl methacrylate

EXAMPLE 4.1

Copolymerization of 2-oxo-1,3-dioxolan-ylmethyl methacrylate and methyl methacrylate 50 mmol of methyl methacrylate, 2.63 mmol of 2-oxo-1,3-dioxolan-4-ylmethyl methacrylate and 1.08 mmol of azoisobutyronitrile in methyl ethyl ketone were initially introduced under a nitrogen atmosphere into a heated flask. The copolymerization was initiated by immersion in an oil bath pre-heated to 75° C. After 2.5 hours, the reaction was stopped by immersion in an ice bath. Dichloromethane was added to the reaction mixture, stirring was effected for 1 hour and the prepolymer formed was precipitated with n-pentane. The polymer was dried for 24 hours in a vacuum drying oven at 50° C. Yield 90% of theory; $M_n$ (GPC) 13 600; $M_w/N_n$=7.8.

The polymer thus prepared was reacted with dodecylamine, 3-dimethylamino-1-propylamine and with a mixture of the two amines.

Polymer-analogous Reaction with Dodecylamine:

300 mg of copolymer (this corresponds to 2.876 mmol of repeating units and hence 0.144 mmol of repeating units can be subjected to a polymer-analogous reaction) and 0.719 mmol of dodecylamine in tetrahydrofuran were initially introduced under a nitrogen atmosphere into a heated Schlenk tube. Stirring was effected at RT. After 24 h precipitation was effected in pentane. The residue was taken up in methylene chloride and extracted three times with 1 molar sodium hydroxide solution. The organic phase was precipitated again in pentane and dried for 24 h in a vacuum drying oven at 50° C. The reaction took place quantitatively.

Polymer-analogous Reaction with 3-dimethylamino-1-propylamine:

300 mg of copolymer (this corresponds to 2.876 mmol of repeating units and hence 0.144 mmol of repeating units can be subjected to a polymer-analogous reaction) and 0.719 mmol of 3-dimethylamino-1-propylamine in tetrahydrofuran were initially introduced under a nitrogen atmosphere into a heated Schlenk tube. Stirring was effected at RT. After 24 h precipitation was effected in pentane. The residue was taken up in methylene chloride and extracted three times with 1 molar sodium hydroxide solution. The organic phase was precipitated again in pentane and dried for 24 h in a vacuum drying oven at 50° C. The reaction took place quantitatively.

Polymer-analogous Reaction with 3-dimethylamino-1-propylamine and Dodecylamine (1:1):

300 mg of copolymer (this corresponds to 2.876 mmol of repeating units and hence 0.144 mmol of repeating units can be subjected to a polymer-analogous reaction), 0.072 mmol of 3-dimethylamino-1-propylamine and 0.072 mmol of dodecylamine in tetrahydrofuran were initially introduced under a nitrogen atmosphere into a heated Schlenk tube. Stirring was effected at RT. After 24 h precipitation was effected in pentane. The residue was taken up in methylene chloride and extracted three times with 1 molar sodium hydroxide solution. The organic phase was precipitated again in pentane and dried for 24 h in a vacuum drying oven at 50° C. The reaction took place quantitatively.

EXAMPLE 4.2

Copolymerization of 2-oxo-1,3-dioxolan-4-ylmethyl methacrylate, 2-phenoxycarbonyloxyethyl methacrylate and methyl methacrylate

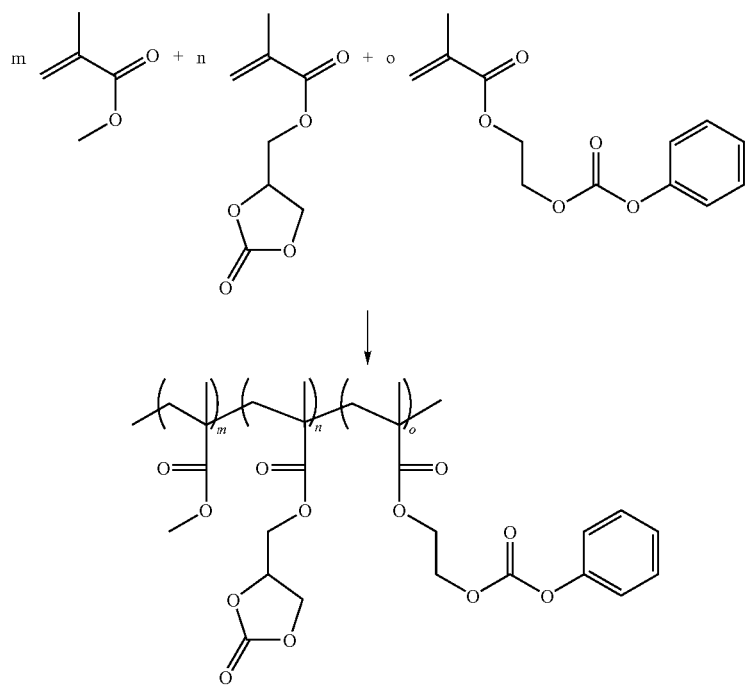

12 mmol of methyl methacrylate, 1.5 mmol of 2-oxo-1,3-dioxolan-4-ylmethyl methacrylate, 1.5 mmol of 2-phenoxycarbonyloxyethyl methacrylate (prepared by reacting hydroxyl ethyl methacrylate with phenyl chloroformate according to V. P. Joshi, S. K. Karode, M. G. Kulkarni, R. A. Mashelkar, *Chem. Eng. Sci.* 1998, 53, 2271) and 0.371 mmol of azoisobutyronitrile in methyl ethyl ketone were initially introduced under a nitrogen atmosphere into a heated flask. The copolymerization was initiated by immersion in an oil bath preheated to 75° C. After 3 hours the reaction was stopped by immersion in an ice bath. Dichloromethane was added to the reaction mixture, stirring was effected for 1 hour and the polymer formed was precipitated with n-pentane. The polymer was dried for 24 hours in a vacuum drying oven at 50° C. Yield 85% of theory; $M_n$ (GPC) 9000; $M_w/N_n$=2.9.

The invention claimed is:

1. A process for modifying a substrate having one or more functional groups selected from hydroxyl groups and primary and secondary amino groups, the process comprising contacting at least one substrate, which is selected from the group consisting of a biomolecule, a polymer and a surface, with a compound of formula I or II under conditions such that the functional groups react, with opening of the 1,3-dioxolane ring or 1,3-diazaheptane ring and formation of a covalent bond, with the compound of formula I or II

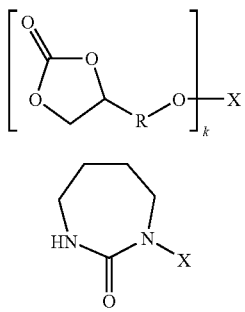

in which
X is CO—NH—R¹ and;
R is $C_1$-$C_{12}$-alkylene; and
k is an integer from 1 to 10,000, inclusive; and
R¹ is ammonio-$C_1$-$C_{30}$-alkyl.

2. The process of claim 1, wherein the substrate is a polymer.

3. The process of claim 1, wherein k is 1.

4. The process of claim 1, wherein the compound of the formula I or II is contacted with a first substrate under conditions such that a covalent bond forms between a first end of the compound of the formula I or II and the first substrate, then the reaction product is contacted with a second substrate under conditions such that a covalent bond forms between a second end of the compound of the formula I or II and the second substrate.

5. The process of claim 4, wherein at least one of the first or second substrate is selected from the group consisting of biomolecules, polymers and surfaces.

6. The process of claim 5, wherein at least one polymer is selected from the group consisting of polyalkyleneamines, polyvinylamine, polyallylamine, polyethylenimine, chitosan, polyamide/epichlorohydrin resins, polyaminostyrene, peptides and proteins.

7. A modified polymer obtained by the process of claim 2.

8. A finish, dispersant, emulsifier, adhesion promoter, adhesive or contact adhesive for modifying surfaces or for immobilizing active substances comprising the polymer of claim 7.

9. A process for modifying a substrate having one or more functional groups selected from hydroxyl groups and primary and secondary amino groups, the process comprising contacting at least one substrate with a compound of fonnula I under conditions such that the functional groups react, with opening of the 1,3-dioxolane ring and formation of a covalent bond, with the compound of formula I

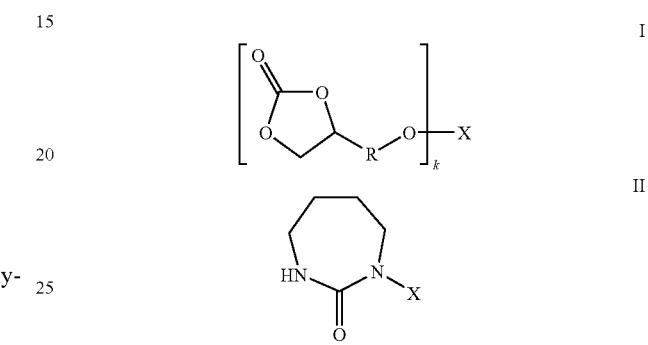

wherein the compound of formula I is selected from the group consisting of
4-phenyloxyearbonyloxymethyl-2-oxo-1,3-dioxolane,
4-(4-phenyloxycarbonyloxy) butyl-2-oxo-1,3-dioxolane, and
4-(vinylsulfonylethoxy)butyl-2-oxo-1,3-dioxolane.

10. A modified polymer obtained by the process of claim 9.

11. A finish, dispersant, emulsifier, adhesion promoter, adhesive or contact adhesive for modifying surfaces or for immobilizing active substances comprising the polymer of claim 10.

* * * * *

UNITED STATES PATENT AND TRADEMARK OFFICE
CERTIFICATE OF CORRECTION

PATENT NO.       : 7,728,069 B2                                      Page 1 of 1
APPLICATION NO.  : 10/582053
DATED            : June 1, 2010
INVENTOR(S)      : Helmut Keul et al.

It is certified that error appears in the above-identified patent and that said Letters Patent is hereby corrected as shown below:

In Claim 9, in column 20, line 32, "4-phenyloxyearbonyloxymethyl-2-oxo-1,3-dioxolane," should read --4-phenyloxycarbonyloxymethyl-2-oxo-1,3-dioxolane,--.

Signed and Sealed this

Thirteenth Day of July, 2010

David J. Kappos
*Director of the United States Patent and Trademark Office*